United States Patent
Stoianovici et al.

(10) Patent No.: US 6,857,609 B2
(45) Date of Patent: Feb. 22, 2005

(54) MEDICAL IMAGING ENVIRONMENT COMPATIBLE POSITIONING ARM

(75) Inventors: Dan Stoianovici, Baltimore, MD (US); Keenan A. Wyrobek, Walnut Creek, CA (US); Dumitru Mazilu, Baltimore, MD (US); Louis L. Whitcomb, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 10/754,779

(22) Filed: Jan. 9, 2004

(65) Prior Publication Data

US 2004/0149874 A1 Aug. 5, 2004

Related U.S. Application Data

(60) Provisional application No. 60/438,953, filed on Jan. 9, 2003.

(51) Int. Cl.$^7$ ............................................. A61B 17/00
(52) U.S. Cl. .................................... 248/276.1; 600/229
(58) Field of Search ............................... 248/104, 160, 248/274.1, 276.1; 600/229

(56) References Cited

U.S. PATENT DOCUMENTS

| | | | | |
|---|---|---|---|---|
| 2,510,198 A | * | 6/1950 | Tesmer | 248/229.25 |
| 3,096,962 A | * | 7/1963 | Meijs | 248/276.1 |
| 3,168,274 A | * | 2/1965 | Street | 248/176.3 |
| 3,529,797 A | * | 9/1970 | Street | 248/160 |
| 3,584,822 A | * | 6/1971 | Oram | 248/160 |
| 3,858,578 A | * | 1/1975 | Milo | 600/229 |
| 5,033,196 A | | 7/1991 | Akin et al. | 33/18.1 |
| 5,447,149 A | * | 9/1995 | Kikawada et al. | 600/229 |
| 5,662,300 A | * | 9/1997 | Michelson | 248/279.1 |
| 5,899,425 A | * | 5/1999 | Corey Jr. et al. | 248/276.1 |

* cited by examiner

Primary Examiner—Anita King
Assistant Examiner—Jon Szumny
(74) Attorney, Agent, or Firm—Larry J. Guffey

(57) ABSTRACT

A positioning arm for positioning and holding a device within a medical imaging environment workspace has: (a) a free-end link in the form of a circular cylinder having a distal end face and an adjoining end face, with the adjoining end face forming a specified angle with the cylinder's centerline and the distal end face adapted to allow for the connection of the device to the free-end link, (b) a plurality of intermediate links, each in the form of a circular cylinder having end faces that form a specified angle with the links' centerline, and each of these intermediate links having a channel connecting their end faces, (c) a base link in the form of a circular cylinder having a base end face and an adjoining end face, with the adjoining end face forming a specified angle with the link's centerline and the base end face adapted to allow for the connection of the arm to a supporting surface, (d) a cable that passes through the link channels so that one cable end attaches to the free-end link and the other end attaches to the base link, and (e) a locking mechanism that attaches to the cable and applies tension to the cable so as to pull adjoining end faces into contact so as to lock them together by frictional, wherein these components are fabricated from MRI compatible materials (e.g., plastics, glass, ceramics, rubbers, composites, and certain non-ferrous metals such as aluminum, titanium, brass, and nitilol).

14 Claims, 5 Drawing Sheets

MEDICAL IMAGING ENVIRONMENT COMPATIBLE POSITIONING ARM

CROSS-REFERENCE TO RELATED APPLICATION

This application claims the benefit of U.S. Provisional Patent Application No. 60/438,953, filed Jan. 9, 2003 by Dan Stoianovici, Keenan Wyrobek, Dumitru Mazilu and Louis L. Whitcomb.

STATEMENT AS TO FEDERALLY SPONSORED RESEARCH

This invention was made with Government support under Grant No. 4 R33 CA88232-02 and entitled "Multi-Imager Compatible Robot For Precise Prostate Access," which was awarded by the National Cancer Institute. The Government may have certain rights in this invention.

BACKGROUND OF THE INVENTION

1. Field of the Invention

This invention relates to geometrical instruments and probe support devices. More particularly, the present invention relates to positioners or holders that are designed to position a small-working-volume instrument, held at the positioner's distal end, at a precise location in a larger work space. One embodiment of the present invention relates to a passive positioning arm that can hold a medical robot or instrument in a medical imagining environment.

2. Description of Prior Art

Many, modern, high precision devices (e.g., medical robots, instruments and tools) have relatively small work volumes or workspaces. A large, work-volume positioner capable of precisely positioning such devices at any location within a specified workspace is needed for the practical implementation of such small-workspace devices.

There exist many commercially available positioners and workpiece holders for these purposes. These positioners usually consist of a number of legs which are held together by various kinds of independently locking connectors and joints. See FIGS. 1A and 1B.

However, these positioners generally do not provide great flexibility in how a workpiece can be moved as it is being positioned from one point to another in a workspace of interest. One apparent solution to this problem would appear to be to add more legs and joints to such existing positioners. However, this solution can quickly become unworkable as the task of independently locking all of the additional joints of such a device becomes exceedingly cumbersome.

This need for positioners which can provide more flexibility in relocating a workpiece or instrument within a larger workspace is especially notable in the field of medicine where such small-workspace devices are constantly being put to use in an ever increasing number of medical procedures. However, a barrier can often exist to the use of commercially available positioners in many of these new medical procedures.

This situation exists because new medical procedures can utilize various real-time, noninvasive, diagnostic imaging techniques to guide the medical practitioner in the performance of the procedure. Thus, for such procedures the environment in which a medical device positioner must operate is a medical imaging environment. Such environments can place exacting requirements on the materials from which medical devices and their positioners may be made.

For example, MRI scanners utilize a strong electromagnet that generates a magnetic field that causes the electrons in a patient's body to spin in a uniform and predictable manner. The diagnostic components of such MRI equipment then manipulates the spinning electrons and uses the resulting information to generate an image of the inside of a patient's body.

However, difficulties are encountered in obtaining accurate images when disruptions and deflections in the scanner's magnetic field are experienced due to the presence in the field of materials (e.g., metals) that produce a magnetic field and/or are susceptible to producing their own magnetic fields when placed within an external magnetic field.

Thus, despite much prior art in the field of positioners and workpiece holders, there still exists a need for further improvements to such devices.

3. Objects and Advantages

There has been summarized above, rather broadly, the background that is related to the present invention in order that the context of the present invention may be better understood and appreciated. In this regard, it is instructive to also consider the objects and advantages of the present invention.

It is an object of the present invention to provide a positioning device that provides greater flexibility in how a workpiece is moved as it is being positioned from one position to another in a workspace of interest.

It is another object of the present invention to provide a positioning device that provides an easier and more convenient means for locking the various elements or legs of such a device into a desired orientation.

It is yet another object of the present invention to provide a positioning device that is compatible with use in a medical imaging environment.

It is still another object of the present invention to provide a positioning arm that can be utilized in a to-be-developed medical robot.

These and other objects and advantages of the present invention will become readily apparent as the invention is better understood by reference to the accompanying summary, drawings and the detailed description that follows.

SUMMARY OF THE INVENTION

Recognizing the needs for the development of improved positioning devices, the present invention is generally directed to satisfying the needs set forth above. In accordance with the present invention, one of these needs can be satisfied by providing an especially designed, positioning device that is suitable for use in a medical imaging environment.

In a preferred embodiment, such a positioning device for positioning and holding a device within a prescribed workspace has: (a) a free-end link in the form of a circular cylinder having a distal end face and an adjoining end face, with the adjoining end face forming a specified angle with the cylinder's centerline and the distal end face adapted to allow for the connection of the device to the free-end link, (b) a plurality of intermediate links, each in the form of a circular cylinder having end faces that form a specified angle with the links' centerline, and each of these intermediate links having a channel connecting their end faces, (c) a base link in the form of a circular cylinder having a base end face and an adjoining end face, with the adjoining end face forming a specified angle with the link's centerline and the base end face adapted to allow for the connection of the arm to a supporting surface, (d) a cable that passes through the link channels so that one cable end attaches to the free-end link and the other end attaches to the base link, and (e) a locking mechanism that attaches to the cable and applies tension to the cable so as to pull adjoining end faces into contact so as to lock them together by frictional, wherein these components are fabricated from MRI compatible materials (e.g., plastics, glass, ceramics, rubbers, composites, and certain non-ferrous metals such as aluminum, titanium, brass, and nitilol).

Thus, there has been summarized above, rather broadly, the present invention in order that the detailed description that follows may be better understood and appreciated. There are, of course, additional features of the invention that will be described hereinafter and which will form the subject matter of any eventual claims to this invention.

DETAILED DESCRIPTION OF THE PREFERRED EMBODIMENT

Figure 1A:
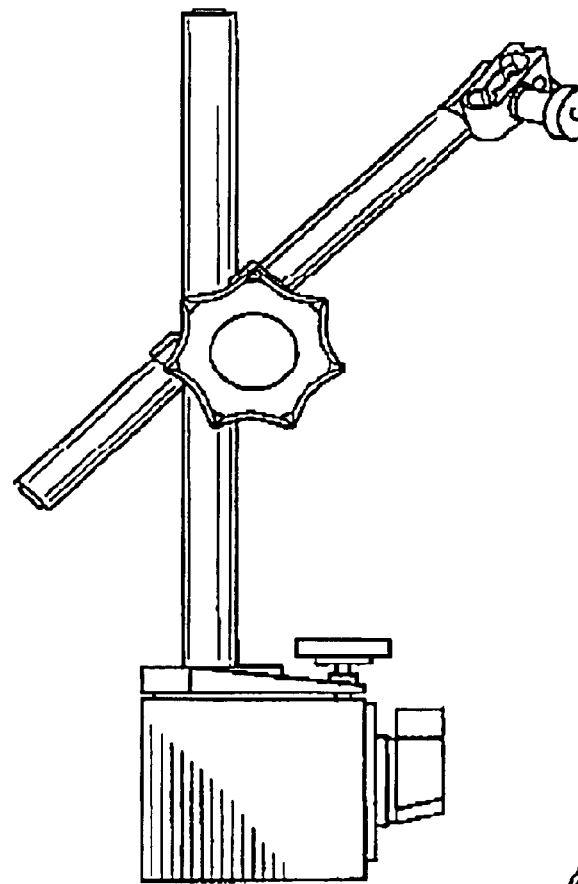
FIGS. 1A and 1B illustrate commercially available positioning devices or workpiece holders.
Figure 1B:
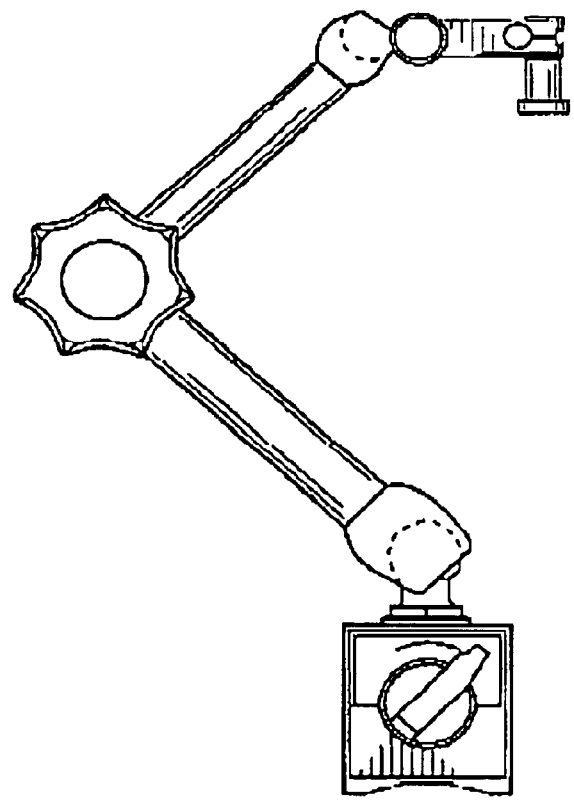

Before explaining at least one embodiment of the present invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

For most medical imaging applications (e.g., X-ray. MRI, ultrasound), the present invention generally relates to positioning devices that are made with materials that have low magnetic susceptibility and produces minimal, if any, magnetic fields. For example, materials such as plastics (e.g., polyetherimide, kevlar, nylon), glass, ceramics, rubbers, etc.

MRI has become the preferred method for high-resolution soft-tissue imaging for pre/post operative diagnosis. Just as X-ray fluoroscopy, first developed for diagnostic imaging, has become an ubiquitous tool for intervention guidance, we conjecture that the next decade will see, with the continued improvement in MRI speed and resolution, the widespread use of MRI for real-time interventional diagnosis and guidance. Thus, a significant needs is expected to exist for MRI compatible intervention devices. As the first step in developing a modular line of MRI compatible clinical devices, we herein report the development of a MRI compatible passive arm for positioning interventional devices within MRI systems.

The materials employed in the construction of the new arm, such as polyetherimide, kevlar, and nylon, ensure that it is MRI safe and it does not induce imaging artifacts. These have been selected for their nonmagnetic, dielectric, and reduced nuclear cross-section.

In a preferred embodiment of the present invention, a positioning arm is disclosed that presents a serial link architecture which is constructed of seven round parts or links of similar geometry. The links are interconnected at the center points of their inclined end faces so as to form six revolute joints, thus rendering a six degree-of-freedom passive arm. An integrated MRI compatible actuator or locking mechanism is used for locking the links of the arm into a desired orientation. The locking actuator may use pneumatic pressure available in all operating rooms. In a preferred embodiment, the air pressure is used to tension a kevlar cord that simultaneously locks all seven links and their six interfacing joints.

Figure 2:
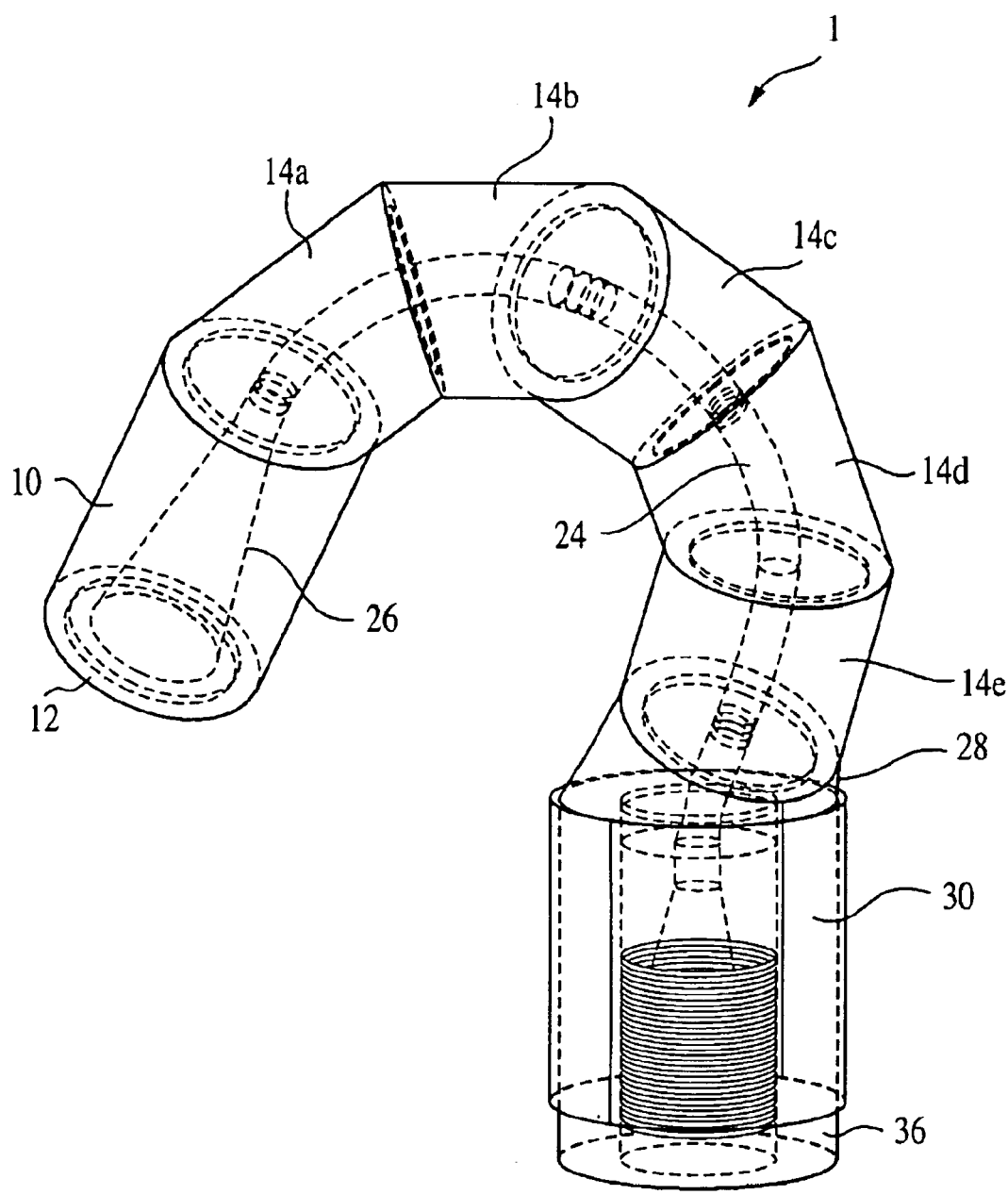
FIG. 2 illustrates a preferred embodiment for a MRI compatible form of the present invention.

FIG. 2 shows a preferred embodiment of a medical imaging environment compatible positioner or positioning arm 1 that is suitable for positioning and holding a medical device or workpiece in place. It consists of circular cylinder pieces or links that are connected end to end and constructed from a high modulus, MRI compatible plastic. A free-end link 10 is adjacent to the device which is to be held. The distal end 12 of this link is adapted to allow the to-be-held device to be connected to this link. Adjacent to the interfacing end of this link is the first of five similarly constructed links 14a–e.

Figure 3:
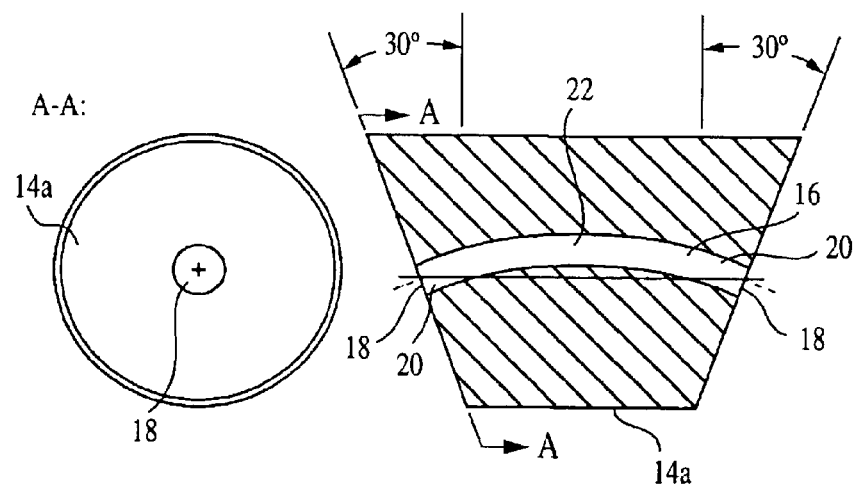
FIG. 3 illustrates a preferred embodiment for the intermediate link of the positioning arm shown in FIG. 2.

FIG. 3 shows a cross-sectional and end view of one of these links 14a–e. Each of these links is formed from a circular cylinder by cutting their end faces so that they form a specified angle with the cylinder's centerline. For the links shown in FIG. 3 these angles have been chosen to be 30 degrees; however, they could been chosen to be any other desired angle (e.g., in the range of 15–45 degrees) so long as the angles between adjoining faces is the same so that the surfaces areas of the adjoining faces are equal.

The smaller these angles are set will obviously affect the degree of movability of a particular link. Consequently, if one wishes to have a positioning arm constructed from small face-angled pieces to fully and precisely cover a large work volume, a greater number of links or pieces will generally be required. The preferred embodiment shown in FIG. 2 has five such pieces or links with faces having 60 degree included angles.

A channel 16 extends between each link's faces. The openings 18 to this channel are face centered at each end. The portions 20 of the channel that are adjacent to the faces are such that the centerline for these portions exits normal to each face of the link. The inner portion 22 of the channel is then contoured so that it forms an arced section which joins the two face-adjacent portions 20. A kevlar cable 24 fits through such channels to connect and eventually lock the links together.

The interfacing end of the free-end link 10 is also seen to be cut at a 30 degree angle to this link's centerline so as to enable it to fully mate with the similarly cut end of link 14a. To terminate the cable 24 in the termination link 10, its fibers are splayed in a cone 26 into which a polystyrene monomer resin is poured and cured.

Adjacent to the link 14e is a base link 28 which is similar to the other links but has only the end or face which is adjacent link 14e cut at a 30 degree angle to the base link's centerline. The other face is normal to the link's centerline.

Next to the base link face which is normal to the link's centerline is a locking link 30. The purpose of this link is to provide the means for pulling taut the cable 24 which connects the links so as to lock each of them into a desired orientation, such as that shown in FIG. 2. There are many well known ways in which this locking task may be accomplished and all of these are considered to come within the scope of the present invention.

Figure 4:
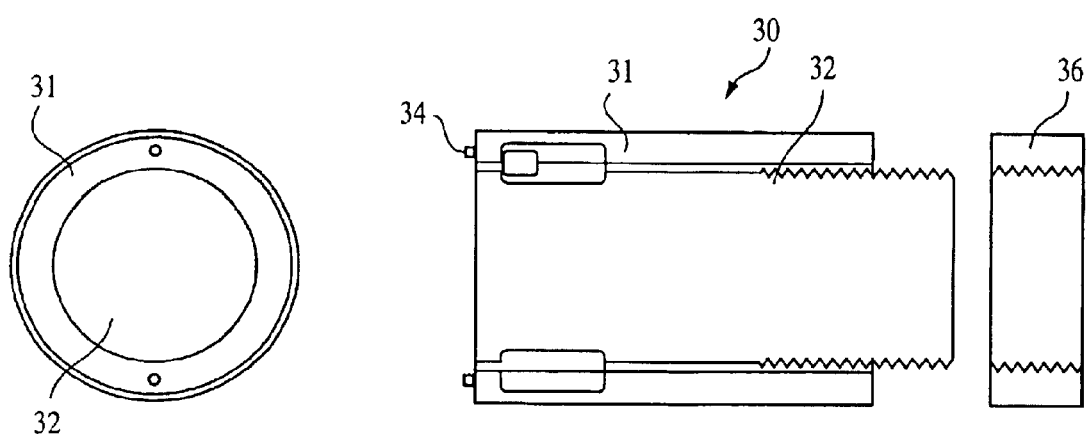
FIG. 4 illustrates a preferred embodiment for a locking mechanism suitable for use with the positioning arm shown in FIG. 2.

FIG. 4 shows a locking link 30 which consists of a cylindrical tube 31 into which is slidably fitted a threaded screw 32 to which the end of cable 24 is attached. Pins 34 extend from the face of the tube adjacent the base link 28 so as to lock these adjoining faces together. A nut 36 is used to pull the screw 32 away from the base link 28 and thus to tension the cable connecting the links.

To operate this positioning arm 1, one merely loosens the arm's locking mechanism so as to reduce the tension in the cable 24 to allow one to rotate and position the various links about their adjoining faces. Tensioning the cable again immediately locks all of the links into their new desired orientations. By adding additional links of varying lengths and prescribed face angles to the present invention, it can be used to position with considerable freedom of movement and then hold a small working-volume device anywhere within a relatively large workspace volume. In those instances in which the workspace is not a medical imaging environment, stronger materials may be used from which to construct the present invention so that it can hold and position heavier devices and work pieces. The same basic arm geometry shown above can be used to construct such a general purpose positioning arm 2.

The use of metals and other non-MRI compatible materials allow for the introduction of several additional features to such a general purpose positioning arm 2. These features include the use of high friction materials which provide advanced locking and higher load bearing capacities.

Figure 5:
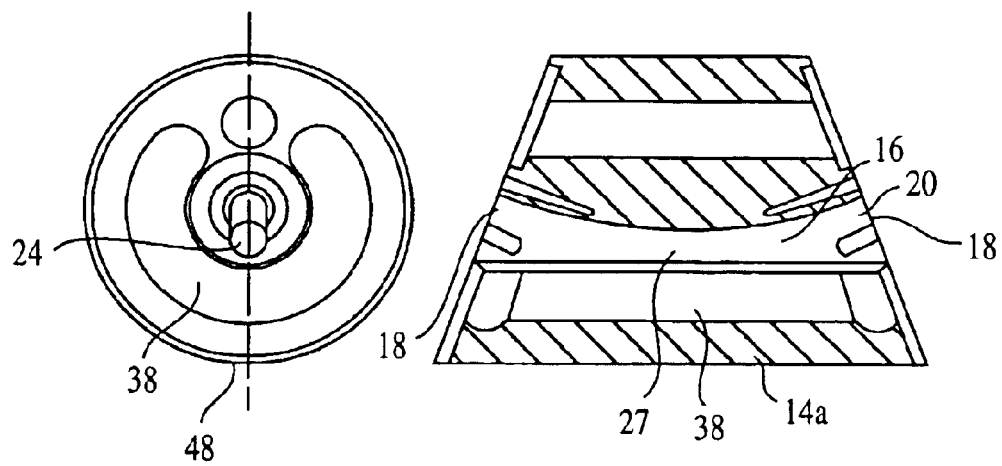
FIG. 5 illustrates a preferred embodiment for the intermediate link of the general purpose positioning arm shown in FIG. 6.

Additionally, an auxiliary channel 38 has been added to this positioning arm to allow the cabling (power and control) required by any held device to be passed through the arm itself. See FIG. 5. Such an auxiliary channel could also be added to the previously disclosed, MRI-compatible, positioning arm.

Figure 6:
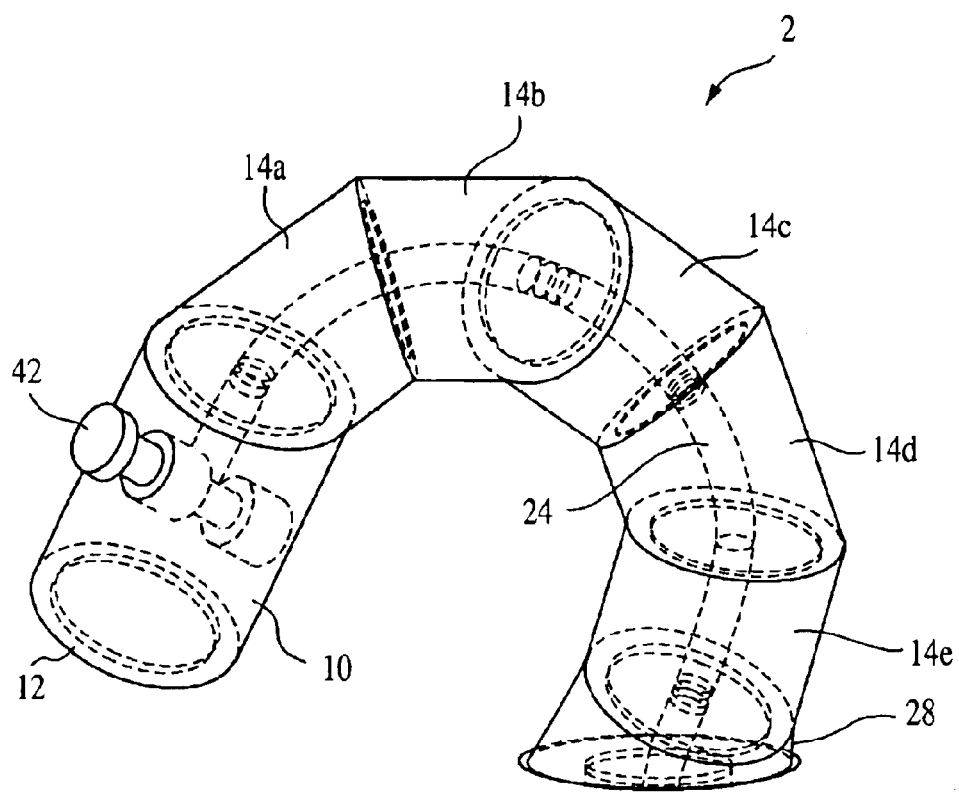
FIG. 6 illustrates a preferred embodiment for a general purpose form of the present invention.

FIG. 6 shows a preferred embodiment of such a general purpose positioning arm 2. In this embodiment, the locking mechanism 40, with its control knob 42, for the arm has been included in the free-end link 10 of the arm so as to possibly make it more convenient to reach by one who is operating the arm. A steel cable 24, which runs down the center of each link, transmits the locking tension and maintains link orientation when the arm is positioned and locked.

Figure 7:
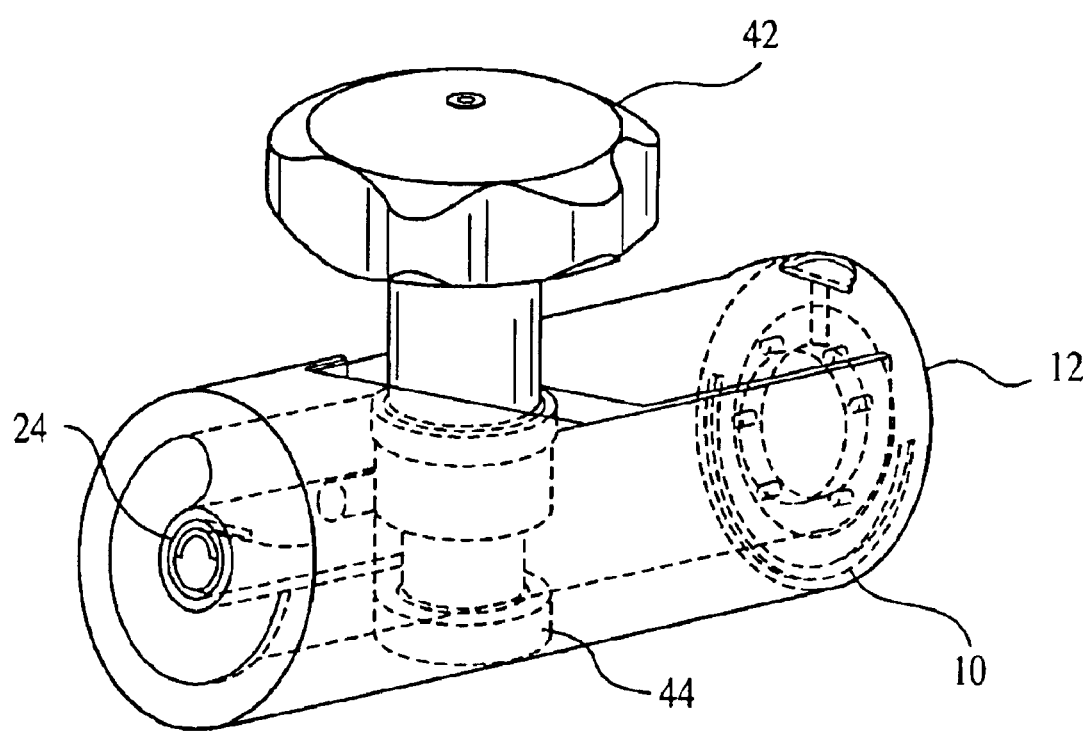
FIG. 7 illustrates a preferred embodiment for a locking mechanism suitable for use with the positioning arm shown in FIG. 6.

A preferred embodiment for this locking mechanism 40, as shown in FIG. 7, uses a simple cam arrangement 44 to tension the cable 24. Although, as previously mentioned, many other locking mechanism are known in the art and are considered to be contained within the scope of the present invention.

As previously mentioned, a channel 38 runs down the length of link in the arm. In order to avoid cutting any cables in the channel, the five similar links alternate in geometry and are limited from rotating the full 360 degrees. Despite such rotation limitations the arm is easily positioned.

Although the foregoing disclosure relates to preferred embodiments of the invention, it is understood that these details have been given for the purposes of clarification only. Various changes and modifications of the invention will be apparent, to one having ordinary skill in the art, without departing from the spirit and scope of the invention.

We claim:

1. A positioning arm for positioning and holding a device within a desired workspace, said arm comprising:

a free-end link having a centerline and a distal end face and an adjoining end face, said adjoining end face being substantially planar and forming a specified angle with said link centerline, said distal end face adapted to allow for the connection of said device to said distal end face, a plurality of intermediate links, each link having a centerline and two end faces, each of said end faces being substantially planar and forming a specified angle with said link centerline, each of said intermediate links having a channel connecting said end faces, a base link having a centerline and a base end face and an adjoining end face, said adjoining end face being substantially planar and forming a specified angle with said link centerline, said base end face adapted to allow for the interfacing of said arm with a supporting surface, a cable having two ends, said cable being passed through said channels so that one end attaches to said free-end link and one end attaches at said base link, and a locking mechanism that attaches to said cable and applies tension to said cable so as to pull adjoining end faces into contact so as to lock by frictional contact said links into a desired orientation, said locking mechanism being attached to one of said links.

2. The positioning arm as recited in claim 1 wherein each of said intermediate links further having an auxiliary channel which allows for cabling connections to be made between said device and power or control means located proximate said base link.

3. The positioning arm as recited in claim 1 wherein the materials of construction for said links, cable and locking mechanism are chosen from those materials that are compatible with a MRI environment.

4. The positioning arm as recited in claim 3 wherein each of said intermediate links further having an auxiliary channel which allows for cabling connections to be made between said device and power or control means located proximate said base link.

5. The positioning arm as recited in claim 3 wherein said specified face angles are set within the range of 15–45 degrees.

6. The positioning arm as recited in claim 5 wherein each of said intermediate links further having an auxiliary channel which allows for cabling connections to be made between said device and power or control means located proximate said base link.

7. The positioning arm as recited in claim 1 wherein the materials of construction for said links, cable and locking mechanism are chosen from those materials that are compatible with a X-ray environment.

8. The positioning arm as recited in claim 7 wherein said specified face angles are set within the range of 15–45 degrees.

9. The positioning arm as recited in claim 8 wherein each of said intermediate links further having an auxiliary channel which allows for cabling connections to be made between said device and power or control means located proximate said base link.

10. The positioning arm as recited in claim 7 wherein each of said intermediate links further having an auxiliary channel which allows for cabling connections to be made between said device and power or control means located proximate said base link.

11. The positioning arm as recited in claim 1 wherein said specified face angles are set within the range of 15–45 degrees.

12. The positioning arm as recited in claim 11 wherein each of said intermediate links further having an auxiliary channel which allows for cabling connections to be made between said device and power or control means located proximate said base link.

13. The positioning arm as recited in claim 1 wherein said specified face angles are set at approximately 30 degrees.

14. The positioning arm as recited in claim 13 wherein each of said intermediate links further having an auxiliary channel which allows for cabling connections to be made between said device and power or control means located proximate said base link.

* * * * *